United States Patent [19]

Bupp et al.

[11] 4,400,618

[45] Aug. 23, 1983

[54] METHOD OF DETECTING AND ANALYZING DAMAGE IN PRINTED CIRCUIT BOARDS

[75] Inventors: James R. Bupp, Endwell; Lawrence R. Maier, Johnson City, both of N.Y.

[73] Assignee: International Business Machines Corporation, Armonk, N.Y.

[21] Appl. No.: 290,632

[22] Filed: Aug. 6, 1981

[51] Int. Cl.³ .................. C09K 11/06; G01N 19/08; G01N 21/16

[52] U.S. Cl. .................. 250/302; 73/762; 73/769; 252/301.19

[58] Field of Search ............. 204/159.23; 250/302; 73/762, 769

[56] References Cited

U.S. PATENT DOCUMENTS

| | | | |
|---|---|---|---|
| Re. 26,888 | 5/1970 | Alburger | 252/301.2 |
| 3,543,570 | 12/1970 | Fijalkowski | 73/104 |
| 3,672,942 | 6/1972 | Neumann et al. | 117/62.2 |
| 3,803,485 | 4/1974 | Crites et al. | 73/799 |
| 3,896,664 | 7/1975 | Alburger | 250/302 |
| 3,929,664 | 12/1975 | Alburger | 250/302 |
| 3,958,119 | 5/1976 | Shigekawa | 250/302 |
| 3,981,185 | 9/1976 | Molina | 250/302 |
| 4,037,466 | 7/1977 | Alburger | 73/104 |
| 4,165,400 | 8/1979 | DeMarco | 427/295 |
| 4,237,379 | 12/1980 | Deckert | 250/302 |

*Primary Examiner*—John C. Bleutge
*Assistant Examiner*—A. H. Koeckert
*Attorney, Agent, or Firm*—Gerald R. Gugger

[57] ABSTRACT

A method of detecting flaws in a printed circuit board laminate having drilled holes wherein a penetrating solution containing a UV fluorescing dye is applied to the laminate to fill the drilled holes and flaws. Excess penetrating solution is removed from the drilled holes and the surface of the laminate. The penetrating solution remaining in the flaws is cured into an insoluble solid and then the laminate is cross-sectioned to provide at least one sample carrying the cured solution. The sample is encapsulated in a clear epoxy and the encapsulated sample is ground and polished to provide a surface which is examined under UV light.

6 Claims, No Drawings

METHOD OF DETECTING AND ANALYZING DAMAGE IN PRINTED CIRCUIT BOARDS

BACKGROUND OF THE INVENTION

In the manufacture of printed circuit boards, a composite of fiber glass and epoxy is provided to which metallized circuitry, usually formed of copper, is applied. The board may be a two sided board having circuitry on the top and bottom sides or it may be a laminated multilayer board which also contains internal signal lines and power planes separated by layers of the dielectric material. The boards are provided with through via holes and interstitial via holes to interconnect the various circuit lines and power planes. These holes are drilled using mechanical or other means followed by a chemical hole clean operation and then plating.

The fiber glass and epoxy composite consists of woven glass cloth embedded in the epoxy and the cloth includes thin glass fibers some of which are hollow. It has been found that during the drilling operation, regardless of the board thickness, fractures, cracks, fiber glass—epoxy separation, ruptured circuit lands, etc., will occur. The drilling action disturbs the fiber glass—epoxy interface resulting in damage. This is particularly true where the drilling goes through glass fibers which cross each other. Also, the hole cleaning operation after drilling may cause additional damage. If these damage defects are allowed to remain, subsequent hole cleaning, seeding, and plating solutions will become entrapped and subsequently copper migration occurs along the damaged areas and also through hollow glass fibers to cause shorts with circuit lines.

Techniques are known in the industry for detecting small flaws, cracks, and discontinuities in composites, test bodies, parts, etc., which may be constructed of metal, ceramic, or other material. Probably the most widely known and used technique involves the application of a liquid penetrant containing a fluorescent dye to the surface of the part to be inspected such that the penetrant solution will enter into the flaws or cracks and will be entrapped therein. Excess penetrant is washed from the surface of the part and then the part is viewed under appropriate lighting, such as "black light" where the fluorescent dye will give a color indication of the location and extent of the surface flaws. Some examples of this technique are disclosed in U.S. Pat. Nos. Re 26,888; 3,543,570 and 4,237,379. In the known prior art teachings relating to this technique, the entrapped penetrant solution remains in a liquid state and the surface to which the penetrant has been applied is inspected. This is satisfactory for many applications where only the outer surface of the part is examined to determine the nature of the flaw or damage. However, it is not satisfactory for the present application where it is necessary to examine the inner surface or wall of a drilled hole to determine the damage, if any, done by the drilling action. It was found that the existing techniques had to be expanded and improved to enable the part to be inspected to be cut or sliced so that a cross-sectional view of the drilled hole could be examined.

SUMMARY OF THE INVENTION

To arrive at the present novel and improved method which is capable of detecting and analyzing damage occuring in holes drilled in a printed circuit board laminate, it was determined that the following conditions would have to be satisfied:

1. A penetrant material must be used which is liquid in order to easily fill irregularly shaped defects.
2. The liquid must have low viscosity for ease of impregnation.
3. The liquid must have low vapor pressure in order to be used in conjunction with a vacuum process which evacuates trapped liquid and gases (air) from the defects.
4. The liquid must wet the laminate.
5. The liquid must contain sufficient fluorescing dye to disclose defects as small as 0.5 microns when illuminated with UV light.
6. The liquid must be polymerizible into a tough insoluble solid that is not diluted, degraded, or removed during subsequent X or Z sectioning processes which includes potting, grinding, polishing, etc.

To meet the above conditions, a polymerizible polymer without a solvent carrier is used and which is in the form of a low-viscosity, ultra-thin anerobic liquid penetrant. A suitable fluorescent dye is mixed with the penetrant and the solution is applied to a drilled laminate while under a vacuum. The vacuum is used to draw air or gas out of the flaws. Upon release of the vacuum, atmospheric pressure will cause the low-viscosity mixture to penetrate into fractures, cracks, voids, fiber glass-epoxy separations, etc., which are present in the laminate. Excessive liquid is removed from the laminate and the impregnated mixture is cured at ambient temperature conditions for periods up to 24 hours or by elevating the ambient temperature in an oven to lessen the curing cycle to provide a tough insoluble solid.

After curing, the laminate is cross-sectioned into sample cut sections which are to be inspected. Each cut section before inspection is encapsulated in a clear epoxy material and the surface to be inspected is ground and polished to establish a better view. The cross-sectioning is done because it is desired to look at the inside of the laminate. The curing of the penetrant is carried out prior to cross-sectioning because if the penetrant is left as a solution, cutting debris would enter into the flaws. The grinding and polishing provides the required flat surface for the subsequent microscopic examination under UV light. The surface may also be photographed to provide a good visual record for further analysis without the need for a microscope.

Accordingly, a primary object of the present invention is to provide a novel and improved method for detecting and analyzing damage in composites.

A further object of the present invention is to provide a novel and improved method for detecting and analyzing damage in printed circuit boards having drilled holes.

A still further object of the present invention is to provide a novel and improved method for detecting and analyzing flaws in drilled holes of a printed circuit board wherein the flaws are impregnated with a polymerizable penetrating solution containing a dye, the impregnated mixture is cured, and the cured portion is examined under ultraviolet light.

A further object of the present invention is to provide a novel and improved method for detecting and analyzing flaws in a printed circuit board wherein a polymerizable penetrating solution containing a dye is applied to the board, excess penetrating solution is removed, the remaining penetrating solution within the board is cured, the board carrying the cured solution is cross-sectioned, and the resulting cross-sections are examined under UV light.

The foregoing and other objects, features and advantages of the invention will be apparent from the following more particular description of a preferred embodiment of the invention:

DESCRIPTION OF PREFERRED EMBODIMENT

In the present method of detecting and analyzing damage in a printed circuit board laminate having drilled holes, a polymerizable polymer without a solvent carrier is used and which is in the form of a low-viscosity, ultra-thin anerobic penetrant solution. A suitable fluorescent dye is mixed with the penetrant solution. Since the circuit board laminate contains epoxy which itself fluoresces somewhat in the blue range, a fluorescing yellow dye is preferrably used which will provide a bright and distinct indication when subjected to UV light. The drilled laminate is then submerged in the penetrant solution in a vat in a vacuum tank and, while submerged, evacuation is carried out at a pressure of 0.3–1.0 Torr for a period of approximately 10 minutes, during which time trapped liquid and gases (air) are evacuated from flaws and damage defects. The vacuum is then released allowing air to bleed back into the tank and atmospheric pressure will force the low-viscosity solution into any cracks, voids, fiber glass-epoxy separations, etc., in the laminate.

The laminate is removed from the tank and excessive liquid is removed from the laminate by rinsing with water, or by air blow-off of excess liquid, or by blotting the surface of the liquid. However done, care is taken so as to not remove any of the liquid trapped in the cracks, voids, fiber glass-epoxy separations, etc. The remaining dye impregnated penetrant solution is then cured either under ambient temperature conditions for periods up to 24 hours or by elevating the ambient temperature in an oven to lessen the curing cycle to provide a tough insoluble solid. For example, curing in an air flow oven at 70° C. for 1 hour provides excellent results. Since the penetrant solution is anerobic, all of the solution in the cracks, etc., will cure due to the absence of air; however, the drilled holes are subjected to air and any penetrant solution therein which did not get washed out will not cure.

After curing, the laminate is cross-sectioned by using a saw, or router, or other suitable means to provide one or more samples which, for example, may be 1 inch square in size. The sample is then placed in a re-usable mold and filled with a suitable clear encapsulating epoxy. The encapsulated sample is ground and polished to provide a flat surface for subsequent microscopic examination under UV light and photographing. The encapsulating epoxy serves to hold the sample and also to fill the drilled holes so that grinding and polishing does not leave any debris pushed into the surface to be examined.

The sample is given a microscopic examination under UV light which will cause the yellow dye to fluoresce to give an visual indication of the location and nature of the damage cracks, etc. It is also desirable to photograph the surface being examined to provide a record which may be further analyzed without the need for a microscope and a UV light source. In photographing the surface, it is desirable to not only pick up the damage flaws which contain the penetrant and fluorescing dye but also the copper circuit lands and lines which do not fluoresce. This may be done by using a double exposure with UV light capturing the flaws and regular light capturing the circuit lands and lines. Also, a broad band bulb or light source could be used to capture both the UV and the visual part of the spectrum. The resulting photograph is particularly useful in that it shows the location of the damage cracks with respect to the location of the circuit lands and lines which gives an indication of the possibility of shorts occuring. In addition, copper plating of the holes could be done before photographing, in which case, damage may be examined and assessed which occur as a result of both the drilling operation and the chemical cleaning operation of the holes.

As was mentioned, the sample cross-section is ground and polished to provide a suitable surface for microscopic and photographic analysis. This analysis will address all damage flaws or cracks which are connected to a drilled hole and which, as a result, are filled with the cured penetrant solution. It may be desired to view a hole looking down into the inside of the hole, or at the inner side wall of the hole, or in both of these directions. For looking down into a hole, the sample is ground and polished in the Z-direction and it may be ground to different depths depending on what internal planes and circuit lines are to be examined. For looking at the inner side wall of a hole, the sample is ground and polished in the X-direction until the middle of the hole is arrived at.

A preferred embodiment of the composition of the penetrant solution used in the present method is represented by the following:

| Formula | Percent by Weight |
| --- | --- |
| Triethylene glycol dimethacrylate | 70 |
| Lauryl methacrylate | 25 |
| Cumene hydroperoxide | 2 |
| Benzoquinone | 1 |
| Fluorescent Yellow "G" dye "Poly-Tergent" B-300 Copper octanoate | 2 |
| Total | 100 |

Triethylene glycol dimethacrylate is an anaerobic monomer capable of forming a cross-linking polymer, i.e. thermosetting. The most desirable monomers for use in anaerobic systems are polymerizable acrylate esters. A general formula and examples are given in U.S. Pat. No. 3,672,942, see col. 4, lines 33 to 43. For example, dipropylene glycol dimethacrylate or tetraethylene glycol dimethacrylate could also be used in the present system.

Lauryl methacrylate is a diluent used to control the properties of the monomer, such as, shrinkage, viscosity, and reactivity. Other reactive diluents such as hydroxyethyl methacrylate could be used. See U.S. Pat. No. 4,165,400, col. 3, lines 48–59.

Cumene hydroperoxide is an initiator which is capable of inducing polymerization in the absence or near absence of oxygen. The most common initiator system is a redox (mutual reduction and oxidation) polymerizable initiator which results in the production of free radicals. Most common are peroxy materials, especially the organic hydroperoxides.

Benzoquinone is an inhibitor which acts as a scavenger for free radicals. It is used to control the amount of reaction that takes place and functions to slow the reaction.

A number of fluorescing dyes could be used; however, Fluorescent Yellow "G", which is a proprietary product of the Morton Norwich Co., is preferred. The dye is yellow in visable light and gives off a bright yellow-green light when irradiated with long wave length ultra violet (black light).

The nonionic surfactant "Poly-Tergent" B-300 is a trademark of the Olin Mathieson Chemical Corp. for a series of nonionic surface active agents consisting of ethoxylated nonyl or octyl phenols. It is used as an emulsifier to remove unreacted material when washed with water. See U.S. Pat. No. 4,165,400, col. 8, for numerous examples of nonionic surfactants.

Copper octanoate is an accelerator which speeds up the reaction. It is used in conjunction with the initiator to form the redox reaction. Accelerators take the form of organic salts of transition metals.

The chemicals mentioned above may be obtained from the Sartomer Co., a division of Sartomer Industries.

It should be pointed out that the specific composition formula set forth above is exemplary of a preferred embodiment of a penetrate solution suitable for use in the present application and the present invention is not to be limited thereby. The percent by weight of the constituents may be varied depending on the characteristics of the penetrant desired. Also, the alternative chemicals mentioned may be substituted for the chemicals set forth in the formula for particular applications.

While the invention has been particularly shown and described with reference to a preferred embodiment thereof, it will be understood by those skilled in the art that various changes in form and details may be made therein without departing from the spirit and scope of the invention.

What is claimed is:

1. A method of detecting flaws in a printed circuit board laminate having drilled holes comprising:
    applying a penetrating solution containing multifunctional methylacrylates and a UV fluorescing dye to said circuit board laminate to fill drilled holes and flaws therein, said penetrating solution being capable of being polymerized;
    removing excess penetrating solution from the drilled holes and the surface of said circuit board laminate;
    curing the penetrating solution remaining in the flaws into an insoluble solid;
    cross-sectioning the circuit board laminate to provide at least one sample carrying the cured solution;
    encapsulating the sample in a clear epoxy;
    grinding and polishing said encapsulated sample to provide a surface to be examined; and
    examining said surface under UV light.

2. The method of claim 1 wherein the penetrating solution is stable in the presence of oxygen and is polymerizable in the absence of oxygen.

3. The method of claim 1 wherein said surface to be examined is photographed under UV light to make a record showing the nature and location of the flaws.

4. A method of detecting and analyzing flaws in a printed circuit board laminate having metallized circuit lines and lands and drilled holes comprising:
    applying a penetrating solution containing multifunctional methylacrylates and a UV fluorescing dye to said circuit board laminate to fill drilled holes and flaws therein, said penetrating solution being capable of being polymerized;
    removing excess penetrating solution from the drilled holes and the surface of said circuit board laminate;
    curing the penetrating solution remaining in the flaws into an insoluble solid;
    cross-sectioning the circuit board laminate to provide at least one sample carrying the cured solution;
    encapsulating the sample in a clear epoxy;
    grinding and polishing said encapsulated sample to provide a surface to be examined;
    examining said surface under UV light; and
    photographing said surface to be examined under both UV light and regular light to make a record showing the nature and location of the flaws which fluoresce and also the metallized circuit lines and lands which do not fluoresce.

5. The method of claim 4 wherein said penetrating solution contains, in percentage by weight, about 70% of an anaerobic monomer, about 25% of a diluent, about 2% of an initiator, about 1% of an inhibitor, and about 2% total of a fluorescing dye, a nonionic surfactant, and an accelerator.

6. The method of claim 4 wherein said penetrating solution contains, in percentage by weight, about 70% of triethylene glycol dimethacrylate, about 25% of lauryl methacrylate, about 2% of cumene hydroperoxide, about 1% of benzoquinone, and about 2% total of yellow "G" dye, "Poly-Tergent" B-300, and copper octanoate.

* * * * *